United States Patent
Horn

(10) Patent No.: US 6,680,619 B1
(45) Date of Patent: Jan. 20, 2004

(54) SENSORING DEVICE FOR MONITORING POTENTIAL ON CORROSION THREATED OBJECTS

(75) Inventor: Harald Horn, Trondheim (NO)

(73) Assignee: Corrocean ASA, Trondheim (NO)

(*) Notice: Subject to any disclaimer, the term of this patent is extended or adjusted under 35 U.S.C. 154(b) by 0 days.

(21) Appl. No.: 09/926,024

(22) PCT Filed: Feb. 14, 2000

(86) PCT No.: PCT/NO00/00054

§ 371 (c)(1),
(2), (4) Date: Aug. 16, 2001

(87) PCT Pub. No.: WO00/50907

PCT Pub. Date: Aug. 31, 2000

(30) Foreign Application Priority Data

Feb. 22, 1999 (NO) ............................................. 19990819

(51) Int. Cl.⁷ ............................................... G01R 27/08
(52) U.S. Cl. ......................................................... 324/700
(58) Field of Search ................................ 324/700, 516, 324/517, 518, 357, 358, 425, 559, 557, 71.1, 71.2, 713, 699, 718

(56) References Cited

U.S. PATENT DOCUMENTS

| | | | |
|---|---|---|---|
| 4,543,528 A | * | 9/1985 | Baraona ........................ 324/262 |
| 4,857,831 A | | 8/1989 | Davies et al. ................. 324/357 |
| 4,982,154 A | | 1/1991 | Schwabe et al. ............. 324/761 |
| 5,486,767 A | | 1/1996 | Schwabe et al. ............... 55/357 |
| 5,864,229 A | * | 1/1999 | Lund ............................ 324/240 |

FOREIGN PATENT DOCUMENTS

WO  86/02728  5/1986

* cited by examiner

*Primary Examiner*—John E. Chapman
*Assistant Examiner*—James Kerveros
(74) *Attorney, Agent, or Firm*—Dennison, Schultz & Dougherty

(57) ABSTRACT

A sensor device for registering voltage drops on corrosion exposed structures and coupled to a surface area thereof to which a voltage is supplied by electrodes causing an excitation current in that area and having a plurality of cables connected to a plurality of sensors arranged in a matrix defining measurement points with defined distances.

10 Claims, 2 Drawing Sheets

SENSORING DEVICE FOR MONITORING POTENTIAL ON CORROSION THREATED OBJECTS

The invention concerns a sensor device for registering voltage levels on corrosion exposed structures. These structures may be pipes and supports in offshore environments, to which a voltage is supplied so that an excitation current flows in the structure. The invention also concerns a method for performing measurements with such a sensor device. The device may be utilized for detection of internal and external corrosion, crack formation, erosion and other defects.

BACKGROUND OF THE INVENTION

NO patent No. 150 136 teaches a method and a device for monitoring steel constructions in order to detect defects, e.g. cracks. By this system fixed measuring points are utilized to register voltage drops when an excitation current is supplied. By comparing the voltage drop at a certain site and a certain time with previously registered measurements at the same site, any development of defects to both sides of the measuring area can be detected.

However, in some cases, it is not convenient to perform measurements with such fixed measuring points, both due to the measuring points themselves, which need to be attached at several places, and due to their connections. The attachment of fixed measuring points may involve welding, which is undesirable in areas where there is a danger of explosion.

SUMMARY OF THE INVENTION

It is therefore a main objective of the present invention to provide a convenient sensor device for mobile or periodical (portable or semi portable) use at a measurement site, so that welded measurement points are not required.

It is a further objective to provide a sensor device which can be installed and used without safety risks in explosion hazard areas.

It is a particular objective to provide a sensor device with an elongated shape, a low production cost, a low height, and which can easily be assembled.

It is a still further objective to provide a measurement method which does not require a continuos connection of sensors as prescribed in NO 150 136, but which can rely on short time measurements. Singular measurements should permit calculation of wall thickness.

A pliable or jointed band configuration allows for easy adaption of this sensor device to various structures. One embodiment is especially convenient for pipes, while another embodiment is easily adapted for various other structures. Both are easy to set tip and remove.

These structures allow "snapshot" measurements. This gives the particular advantage that it does not require continuous operation, it may be performed in minutes with a free choice of intervals and without any need for measurement equipment and/or connections at the measurement site between each measurement. The intervals may be quite long, e.g. weeks or months.

DETAILED DESCRIPTION OF THE DRAWINGS

Figure 1:
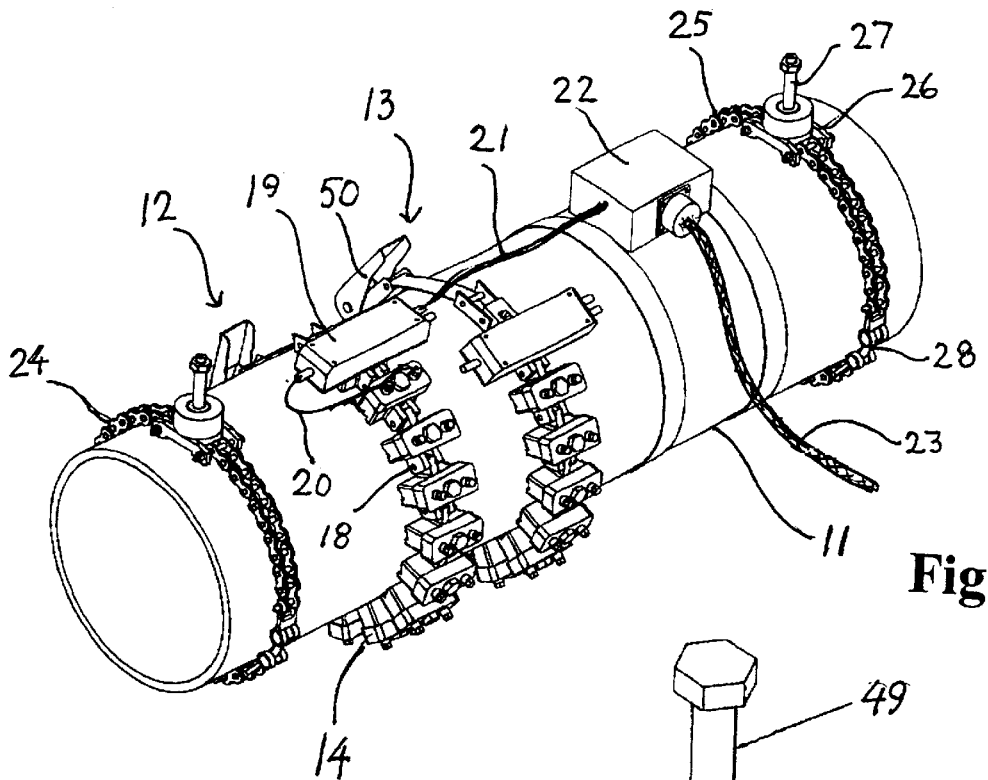
Figure 3:
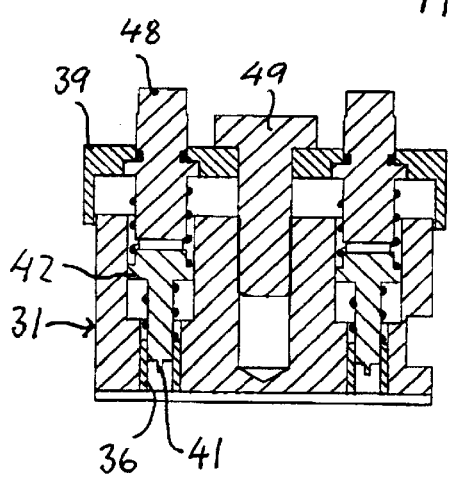
Figure 2:
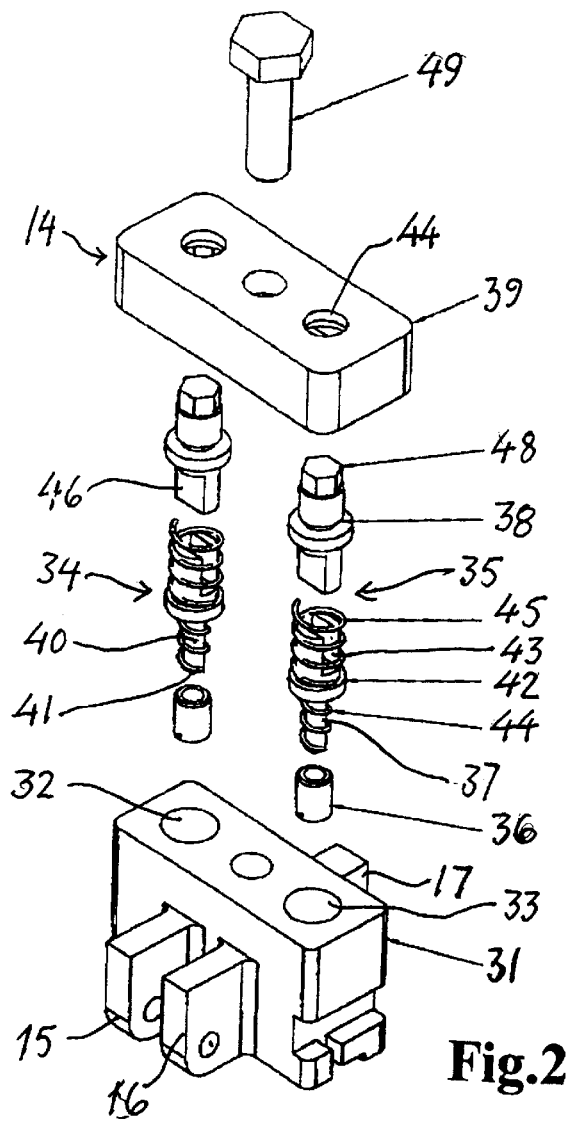
Figures 4, 5:
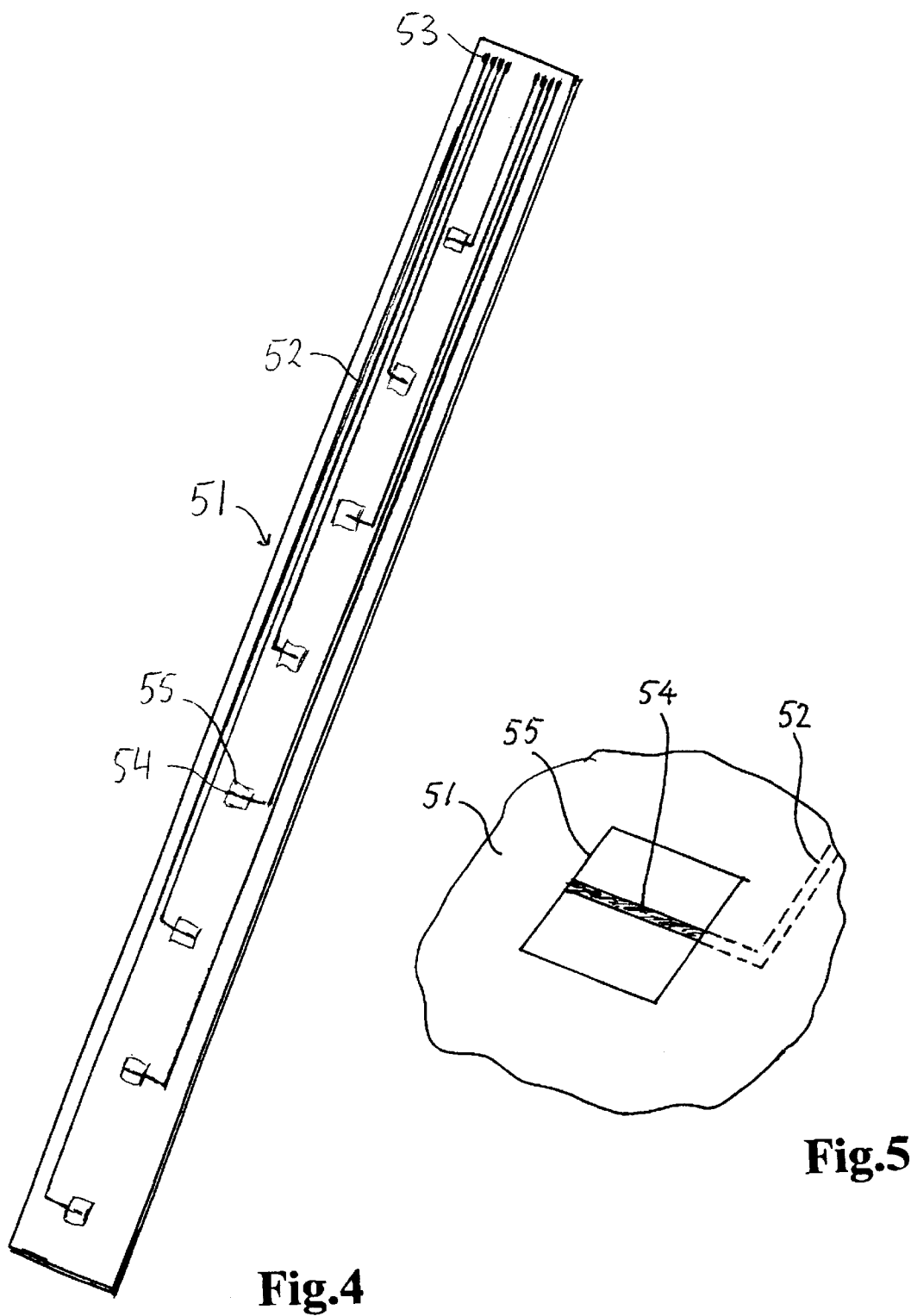

The invention is described in further detail below with reference to the accompanying drawings where FIG. 1 shows a view in perspective of two sensor chains according to a first embodiment of the invention, FIG. 2 shows an exploded view in perspective of a contact joint for the sensor chain of FIG. 1, FIG. 3 shows a section through the contact joint of FIG. 2 in partially assembled condition, FIG. 4 shows a view in perspective of a sensor band according to another embodiment of the invention, seen from the contact side, while FIG. 5 shows a segment of the sensor band according to FIG. 4, illustrating one contact point.

DETAILED DESCRIPTION OF THE INVENTION

In FIG. 1 a section of a steel pipe 11 which may be part of an offshore installation structure is shown. On the pipe 11 two sensor chains 12 and 13 are arranged which extend in band shape around the circumference of pipe 11 at a defined axial distance from each other. Each sensor chain constitutes a number of contact joints 14 with two extending ear members 15, 16 on one side and one extending ear member 17 on another side, the ear members each being provided with a hole for receiving a linkage pin 18 in order to form a chain. A tensioning device 50 is provided in order to hold the sensor chain tightly fit to the pipe 11.

For each sensor chain a connection housing 19 is provided for connecting pairs of cables 20 from each contact joint 14 to a common cable clamp, for connection of a cable 21. The connection housing 19 also contains a printed circuit board that inter alia provides identity signals for each of the measuring sites.

Iinterface circuits are provided that amplify the voltage signals measured between the pins and convert the analogue signals to digital signals that are transmitted to a data logger. In this way a computer can recognize data from the individual measuring points in order to process data from the measured signals. In addition the analogue-to-digital conversion allows the computer equipment needed to analyse the measured signals to be placed in significant distance from the measurement points with no deterioration of the signals. The measured signals may be transmitted by multiplexing.

Cables 21 from several sensor chains are collected in a collecting box 22 for further transmittal by means of a cable 23 to a computer (not shown). This implies few connections and easy assembly of the sensor device, while allowing the computer to be placed at an easily accessible location.

The measurement assembly according to this example also includes two contact chains 24, 25 which are to be fastened around the pipe 11 axially outside the sensor chains 12, 13. Each of the chains 24, 25 comprises an electrode for the supply of an electric voltage, e.g. 10 mV, which gives a current (excitation current) through the pipe 11. Each chain 24, 25 has a connecting joint 26 with a supply terminal 27 for supply of voltage and a clamp member 28 for tightening the contact chains around the pipe.

FIG. 2 shows a preferred embodiment of the design of each contact joint (chain element) 14. In a block element 31 of an electric insulating material, e.g. plastic, with ear members 15–17, two holes 32, 33 are provided for contacting and turning units 34, 35. The contacting and rotating units 34, 35 are identical, with a slide bushing 36, a contact pin 37, and a rotary plug 38 which are covered by a cover 39. The assembly of these parts is shown in FIG. 3.

Each slide bushing 36 is arranged in a cylindrical bore in the block element 31. The contact pins 37 have a stem 40 with a lower edge 41, a ring shaped flange 42 at its middle section and an axial slit 43 downwards from the upper end. Under the ring shaped flange 42 a coil spring 44 is arranged, the lower end of which rests on the slide bushing 36. Over the ring shaped flange 42 an upper coil spring 45 is arranged, the upper end of which is constrained by the cover 39.

The rotary plug 38 has a lower tongue 46 which fits into the slit 43 and a free end 48 which will extend through opening 44 of the cover 39. Free end 48 has an hexagonal shape to fit a spanner. The lower coil spring 46 rests against the slide bushing 36, while the upper coil spring 47 rests against the flange 42. The upper coil spring 47 is harder than the lower coil spring 46, so that the edge 41 of the contact pin 37 is pressed downwards against the measurement object when the cover 39 is lowered by the aid of a bolt 49. Supply cables (not shown) are soldered to the metallic slide bushings 36.

In FIG. 3 a contact joint 14 is shown during assembly, before the cover 39 is fully tightened.

On assembly the contact pins are turned by turning the ends 48 with a spanner, so that an edge of the edge 41 will penetrate any surface coating on the object to be measured, forming a metal to metal contact with no significant transition resistance.

FIG. 4 shows an alternative embodiment of a sensor device according to the invention. Here the pliable support constitutes a band 51 of a plastic material being provided with printed longitudinal conductive paths 52 from a contact area 53 at one end to a series of contact points 54 distributed along the sheet band 51. The conductive paths 52 are covered by a sheet, so that they are inaccessible with the exception of openings 55 (FIG. 5) which expose each contact point 54, i.e. the free end of each conductive path 52.

Such a sensor band can be manufactured efficiently and relatively inexpensivly by use of known materials and techniques. It can be assembled by pressurised gluing so that the paths are fixed to a support and covered under a sheet with the exception of a pressure area at each contact point 54, where an electrically conducting area is formed.

An alternative embodiments a sensor band may be provided with two rows of contact points, e.g. for arrangement over a welding seam or another line where there is enhanced risk of impairment. The same effect can be obtained by arranging two sensor bands with a single row of sensors side by side.

According to the invention, measurements may be performed quite rapidly, in a few minutes, and with intervals in the magnitude of weeks or months between subsequent samples. Such "snapshot" measurements constitute a new method for inspecting the internal condition of pipes. Methods have previously been used for monitoring the condition of a pipe or a structure , by studying the development over time. The condition of the object is registered in a computer at the time of installation, and subsequent measurements is compared with the initial measurement so it becomes possible to calculate e.g. the remaining wall thickness of a pipe at any time in the surveillance period. Such measurements must be based on a series of measurements with duration from a week to some months, in order to enable the system to provide a specified accuracy.

In accordance with the invention the method is now utilised as an inspection tool using short time measurements. For inspection purposes it is of interest to be able to measure at new sites and to obtain a result immediately. The present invention makes this possible, due to use of moveable pin holders that are easy to install and where the distances between the various pairs of pins in the pin matrix are well defined and constant. The measurements provide differential voltages for different pairs of pins in the pin matrix, and these values are used to calculate the wall thickness for each pair of pins, thereby obtaining a picture of the internal corrosion in the area covered by the pin matrix. The wall thickness is calculated as follows:

The resistance for each pair of pins is calculated from measured voltage between the pins with a known excitation current.

The external pipe dimeter is known,

Specific resistance for the relevant material is known or measured (separate measurement), The temperature of the pipe is measured, its temperature coefficient needs to be known.

The formula used for the calculation is principally:

$$R=\rho(1-\Delta Tk)pd/(OD'wt)$$

where

R is resistance for the pair of pins in question, (=diff. pin voltage/ excitation current), $\rho$ is specific resistance for the pipe steel, $\Delta T$ is temperature difference, k is temperature coefficient, OD' is modified external pipe diameter or width of the object wt is wall thickness at the pin pair in question, pd is pin distance Thus the wall thickness can be calculated.

The accuracy of the method is not as good as for the traditional method with measurements in time series, but it has its obvious advantages as a method for inspection and for this purpose the accuracy is sufficient.

What is claimed is:

1. Sensor device for registering voltage drops on corrosion exposed structures having a surface area, comprising:

at least one contact chain having a supply terminal, said at least one contact chain disposed around said structure and said supply terminal in contact with said surface area for providing a voltage, and causing an excitation current in the area, a plurality of sensors arranged in a matrix defining measurement points with defined distances, to obtain signals related to the voltage distribution in the surface area as a basis for determining material thickness and/or structure in the measurement area, in this way determining wall thickness and/or the occurrence of corrosion and/or erosion defects each of said plurality of sensors comprising a support means (14, 52) holding and housing therein a row of contact members (37, 54) said contact members are held in engagement with the surface area of the measured material in the measurement area, wherein from each contact member an electric conductor (20, 52) is led to a cable terminal (19, 53), and wherein that the support means (14, 52) is pliable or multi-articulated, so that the contact members (37, 54) can be brought into engagement with curved surfaces and other non-flat surfaces.

2. Sensor device according to claim 1 for use on pipes, wherein the support means are connected to one another by linkage pins forming a chain, and wherein each support means holds at least one, contact pin (37), under tension by a coil spring.

3. Sensor device according to claim 2, wherein two rows of support means are arranged side by side around the circumference of the pipe, in a way so that they lie on each side of a material splice.

4. Sensor device according to claim 2, characterized in that the contact pins (37) are rotatably shafted and provided with an edge which can be turned for improved engagement with theobject to be measured.

5. Method for inspection measurements of steel constructions that are exposed to corrosion and other forms of deterioration, ship constructions, drilling rigs and bridges, wherein an electric voltage is supplied to provide a current through a measurement area and where measurements of voltage levels are conducted at a plurality of contact points distributed over the area this way assessing the voltage drops between the contact points, characterized in that the measurements are performed with contact points arranged on unprepared surfaces, with a sensor device as defined by claim 2, and that the material thickness is determined by calculation including the following algorithm:

$$R = \rho(1 - \Delta Tk) pd / (OD'wt)$$

where

R is resistance for the pin pair in question, (=diff. pin voltage/excitation current), $\rho$ is specific resistance for the steel, $\Delta T$ is temperature difference, k is temperature coefficient, OD' is modified external pipe diameter or width of the object, wt is wall thickness at the pin pair in question, pd is pin distance.

6. Method according to claim 5, characterized in that an identity code is stored for each measurement point, the result of the measurement is stored in a computer memory, the results of several subsequent measurements with intervals in the magnitude of weeks to months are analysed to assess the occurrence of any changes in the voltage distribution and thereby the condition of the relevant part of the object in question.

7. Sensor device according to claim 1, characterized in that an electric circuit is connected to each contact point or each pair of contact points, converting the analogue measured signal to a digital signal and providing the converted signal with an identity signal for the contact point or contact points in question.

8. Sensor device according to claim 1, further comprising a flexible sheet (51) of an electric non-conducting material into which conductive paths (52) are embedded, leading to a number of distributed and exposed measurement points (54).

9. Sensor device according to claim 8, characterized in that the flexible sheet (51) is band shaped with contact points (54) arranged in a row or alternatively on two parallel rows for localisation over a split structure.

10. Sensor device according to claim 8, characterized in that the conductive paths (52) are printed circuit paths and the contact points are exposed areas at the end of these.

\* \* \* \* \*